United States Patent [19]

Kaeding et al.

[11] 4,086,287
[45] Apr. 25, 1978

[54] SELECTIVE ETHYLATION OF MONO ALKYL BENZENES

[75] Inventors: Warren W. Kaeding, Westfield; Lewis B. Young, Kendall Park, both of N.J.

[73] Assignee: Mobil Oil Corporation, New York, N.Y.

[21] Appl. No.: 706,981

[22] Filed: Jul. 19, 1976

[51] Int. Cl.$^2$ .............................................. C07C 3/52
[52] U.S. Cl. ............................ 260/671 R; 260/671 C
[58] Field of Search ........... 260/671 R, 671 C, 672 T, 260/668 A; 252/455 Z; 423/328

[56] References Cited

U.S. PATENT DOCUMENTS

| | | | |
|---|---|---|---|
| 3,695,209 | 6/1976 | Butter et al. | 260/671 C |
| 3,751,506 | 8/1973 | Burress | 260/671 M |
| 3,856,873 | 12/1974 | Burress | 260/668 A |
| 3,965,207 | 6/1976 | Weinstein | 260/671 C |
| 3,965,208 | 6/1976 | Butter et al. | 260/671 R |
| 4,002,697 | 1/1977 | Chen | 260/671 C |
| 4,011,276 | 3/1977 | Chu | 260/672 T |

OTHER PUBLICATIONS

Masterton et al., *Chemical Principles* 2nd Edition, W. B. Saunders, Phila., Pa. (1969) p. 362.

*Primary Examiner*—O. R. Vertiz
*Assistant Examiner*—Brian E. Hearn
*Attorney, Agent, or Firm*—Charles A. Huggett; Raymond W. Barclay

[57] ABSTRACT

A catalytic process is provided for the ethylation of a mono alkyl benzene wherein the alkyl substituent contains 1 or 2 carbon atoms, i.e. toluene or ethylbenzene, to selectively produce the para ethyl derivative thereof, i.e. para ethyltoluene or para diethylbenzene by contacting said mono alkyl benzene, under conversion conditions, with an ethylating agent in the presence of a catalyst comprising a crystalline aluminosilicate zeolite, which zeolite is characterized by an activity, in terms of alpha value, of between about 2 and about 5000, and preferably between about 20 and about 500, a xylene sorption capacity greater than 1 gram/100 grams of zeolite and an ortho xylene sorption time for 30 percent of said capacity of greater than 10 minutes, said sorption capacity and sorption time being measured at 120° C. and a xylene pressure of 4.5 ± 0.8 mm. of mercury, said catalyst comprising a crystalline aluminosilicate zeolite having a silica to alumina ratio of at least about 12 and a constraint index, as hereinafter defined, within the approximate range of 1 to 12 to yield a resulting product in which the para ethyl derivative of said mono alkyl benzene is present in an amount greater than the thermodynamic equilibrium concentration thereof in the total dialkyl substituted benzenes produced.

15 Claims, No Drawings

SELECTIVE ETHYLATION OF MONO ALKYL BENZENES

BACKGROUND OF THE INVENTION

1. Field of the Invention

This invention relates to a process for selectively converting certain mono alkyl benzenes to para dialkyl benzenes, such as para ethyltoluene or para diethylbenzene, utilizing a specified crystalline aluminosilicate zeolite catalyst.

2. Description of the Prior Art

Alkylation of aromatic hydrocarbons utilizing crystalline aluminosilicate catalysts has theretofore been described. U.S. Pat. No. 2,904,697 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g. benzene with ethylene, in the presence of a ZSM-5 type zeolite catalyst.

While the above-noted prior art is considered of interest in connection with the subject matter of the present invention, the selective ethylation process described herein utilizing a catalyst of a crystalline aluminosilicate zeolite, said zeolite having a silica/alumina ratio of at least about 12 and a constraint index of 1 to 12, which catalyst has undergone prior modification to alter the activity and sorption characteristics thereof to achieve unexpectedly high selective production of para ethyltoluene or para diethylbenzene has not, insofar as is known, been heretofore described.

Both ethyltoluene and diethylbenzene are valuable chemicals. They may be dehydrogenated to produce the corresponding vinyltoluene and divinylbenzene. It has heretofore been recognized that the presence of substantial quantities of the ortho isomers are highly undesirable in the charge undergoing dehydrogenation since they tend to lead to ring closure with formation of the corresponding indenes and indanes which adversely affect the properties of the resultant polymer. The indenes and indanes are difficult to separate from the desired vinyl aromatic products. It has accordingly heretofore been necessary to remove the ortho isomers from the ethyltoluene and diethylbenzene charge stocks by expensive distillation techniques prior to dehydrogenation thereof.

It is evident that the availability of the ethyltoluene or diethylbenzene in which the ortho isomer is initially absent or present only in trace amount would eliminate the necessity for expensive prior removal of this isomer. Such products have, however, not heretofore been available.

SUMMARY OF THE INVENTION

In accordance with the present invention, a process has been discovered for producing ethyltoluene or diethylbenzene virtually free from the undesired ortho isomer, thus eliminating the heretofore necessary expensive purification procedures. Following the teachings of this invention, para ethyltoluene or para diethylbenzene may be selectively produced either as the sole isomer or as the major isomer in admixture with a minor amount of the meta isomer, together with trace amount or none of the ortho isomer.

The process of the invention involves ethylation of a mono alkyl benzene wherein the alkyl substitutent contains 1 or 2 carbon atoms by contacting said mono alkyl benzene with an ethylating agent, under conversion conditions, in the presence of a catalyst having a controlled hexane cracking activity, a minimum diffusion time for ortho-xylene and a minimum xylene sorption capacity. More particularly, the zeolite utilized herein is characterized by an activity, in terms of alpha value, of between about 2 and about 5000, a xylene sorption capacity greater than 1 gram/100 grams of zeolite and an ortho xylene sorption time for 30, percent of said capacity of greater than 10 minutes, where the sorption capacity and sorption time are measured at 120° C and a xylene pressure of 4.5 ± 0.8 mm. of mercury.

In a preferred embodiment, the present process comprises ethylation of toluene or ethylbenzene to yield ethyltoluene or diethylbenzene in which the proportion of the para isomer is substantially in excess of its normal equilibrium concentration and preferably in excess of 50 weight percent of the total ethyltoluene or diethylbenzene product produced in the presence of the specified catalyst. Ethylation is effectively accomplished at a temperature between about 250 and about 600° C. at a pressure of between about 0.1 and about 100 atmospheres utilizing a feed weight hourly space velocity (WHSV) between about 0.1 and about 100. The latter WHSV is based upon the weight of catalyst compositions, i.e. total weight of active catalyst and binder therefor. The molar feed ratio of mono alkyl benzene/ethylating agent is generally between about 1 and about 10.

DESCRIPTION OF SPECIFIC EMBODIMENTS

The mono alkyl benzene undergoing ethylation in accordance with this invention is one wherein the alkyl substituent is methyl or ethyl, i.e. toluene or ethylbenzene. The ethylating agent employed is generally ethylene or a gaseous mixture high in this reactant. Other suitable ethylating agents include ethyl alcohol and ethyl halides, e.g. ethyl chloride, diethyl ether, diethyl sulfide and ethylmercaptan.

In accordance with the present invention, the above described reactants are brought into contact, under conversion conditions, with a bed comprising particleform catalyst containing a crystalline aluminosilicate having: (1) an activity, in terms of alpha value, of between about 2 and about 5000, (2) a xylene sorption capacity greater than 1 gram/100 grams of zeolite and (3) an ortho-xylene sorption time for 30 percent of said capacity of greater than 10 minutes, where the sorption capacity and sorption time are measured at 120° C. and a xylene pressure of 4.5 ± 0.8 mm. of mercury.

The alpha value reflects the relative activity of the catalyst with respect to a high activity silica-alumina cracking catalyst. To determine the alpha value as such term is used herein, n-hexane conversion is determined at about 1000° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as multiple of this standard, i.e. the silica-alumina standard. The silica-alumina reference catalyst contains about 10 weight percent Al$_2$O$_3$ and remainder SiO$_2$. This method of determining alpha, modified as described above, is more fully described in the Journal of Catalysis, Vol. VI, Pages 278-287, 1966.

The measurements of hydrocarbon sorption capacities and rates are conveniently carried out gravimetrically in a thermal balance. In particular, it has been found that an equilibrium sorption capacity of xylene, which can be either para, meta, ortho or a mixture thereof, preferably para-xylene since this isomer reaches equilibrium within the shortest time of at least 1 gram per 100 grams of zeolite measured at 120° C. and a xylene pressure of 4.5 ± 0.8 mm. of mercury and an orthoxylene sorption time for 30 percent of said capacity of greater than 10 minutes (at the same conditions of temperature and pressure) are required in order to achieve the desired selective production of para dialkyl substituted benzenes.

It has been found that zeolites exhibiting very high selectivity for para-dialkylbenzene production require a very long time up to and exceeding a thousand minutes to sorb o-xylene in an amount of 30% of total xylene sorption capacity. For those materials it is more convenient to determine the sorption time for a lower extent of sorption, such as 5%, 10% or 20% of capacity, and to estimate the 30% sorption time by applying the following multiplication factors F as illustrated for 5% sorption:

| $t_{0.3} = F \cdot t_{0.05}$ Percent of sorption capacity | Factor(F) to Estimate 30% Sorption Time |
|---|---|
| 5 | 36 |
| 10 | 9 |
| 20 | 2.2 |

The zeolite catalysts utilized herein are members of a novel class of zeolites exhibiting some unusual properties. The zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indiated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes. However, in all instances, at a temperature within the above-specified range of 550° F to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. Application Ser. No. 528,060, filed Nov. 29, 1974. This zeolite can be identified, in terms of mole ratios of oxides and in the anhydrous state, as follows:

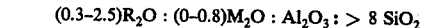

$(0.3–2.5)R_2O : (0–0.8)M_2O : Al_2O_3 : > 8\ SiO_2$ wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

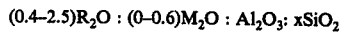

$(0.4–2.5)R_2O : (0–0.6)M_2O : Al_2O_3 : xSiO_2$ wherein R is an organic nitrogen-containing cation derived from a 2-hydroxyalkyl) trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d (A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH−/SiO₂ | 0.05–0.5 | 0.07–0.49 |
| H₂O/OH− | 41–500 | 100–250 |
| SiO₂/Al₂O₃ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH− is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150°

C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

$$(0.4-2.5)R_2O : (0.0.6)M_2O : Al_2O_3 : xSiO_2$$

wherein R is an organic nitrogen-containing cation derived from ethylenediamine or pyrrolidine, M is an alkali metal, especially sodium, and $x$ is from greater than 8 to 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d (A) | I/Io |
|---|---|
| 9.6 ± 0.2 | Very Strong-Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity providing said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The crystalline aluminosilicate zeolites employed are modified prior to use by combining therewith a small amount, generally in the range of about 0.5 to about 40 weight percent, preferably of a difficultly reducible oxide, such as the oxides of phosphorous, boron, magnesium or combinations thereof and also oxides of antimony. Modification of the zeolite with the desired oxide or oxides can readily be effected by contacting the zeolite with a solution of an appropriate compound of the element to be introduced, followed by drying and calcining to convert the compound to its oxide form.

Representative phosphorus-containing compounds which may be used include derivatives of groups represented by $PX_3$, $RPX_2$, $R_2PX$, $R_3P$, $X_3PO$, $(XO_3)PO$, $(XO)_3P$, $R_3P=O$, $R_3P=S$, $RPO_2$, $PPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites. $(RO)PR_2$, and dialkyl alkylphosphonite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain one to four carbon atoms.

Other suitable phosphorous-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphionochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PX$, $(RS)(R)P(S)Cl$ and $R_2P(S)Cl$.

Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchloro thiophosphate, methyl acid phosphate and other alcohol-$P_2O_5$ reaction products.

Reaction of the zeolite with the phosphorus compound is effected by contacting the zeolite with such compound. Where the treating phosphorus compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite such as air or nitrogen or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example, air. Heating can be at a temperature of about 150° C. However, higher temperatures, i.e., up to about 500° C. are preferred. Heating is generally carried out for 3-5 hours but may be extended to 24 hours or longer. While heating temperatures above about 500° C. can be employed, they are not necessary. At temperatures of about 1000° C, the crystal structure of the zeolite tends to deteriorate.

The amount of phosphorus incorporated with the zeolite should be at least about 0.5 percent by weight. However, it is preferred that the amount of phosphorus in the zeolite be at least about 2 percent by weight when the same is combined with a binder, e.g. 35 weight percent of alumina. The amount of phosphorus can be as high as about 25 percent by weight or more depending on the amount and type of binder present. Preferably, the amount of phosphorus added to the zeolite is between about 0.7 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factos being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite with the treatimg compound, and the amount and type of binder incorporated with the zeolite.

Another suitable modifying oxide is that of magnesium. Representative magnesium-containing compounds include magnesium acetate, magnesium nitrate, magnesium benzoate, magnesium proprionate, magnesium 2-ethylhexoate, magnesium carbonate, magnesium, formate, magnesium oxylate, magnesium amide, magnesium bromide, magnesium hydride, magnesium lactate, magnesium laurate, magnesium oleate, magnesium palmitate, magnesium silicylate, magnesium stearate and magnesium sulfide.

Reaction of the zeolite with the treating magnesium compound is effected by contacting the zeolite with such compound. Where the treating compound is a liquid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e. may be used as a neat liquid. Where the treating compound is in the gaseous phase, it can be used by itself or can be used in admixture with a gaseous diluent relatively inert to the treating compound and the zeolite such as helium or nitrogen or with an organic solvent, such as octane or toluene.

Heating of the magnesium compound impregnated catalyst subsequent to preparation and prior to use is preferred. The heating can be carried out in the presence of oxygen, for example, air. Heating can be at a temperature of about 150° C. However, higher temperatures, i.e. up to about 500° C. are preferred. Heating is generally carried out for 1-5 hours but may be extended to 24 hours or longer. While heating temperatures above about 500° C. may be employed, they are generally not necessary. At temperatures of about 1000° C., the crystal structure of the zeolite tends to deteriorate. After heating in air at elevated temperatures, the oxide form of magnesium is present.

The amount of magnesium oxide incorporated in the zeolite should be at least about 0.25 percent by weight. However, it is preferred that the amount of magnesium oxide in the zeolite be at least about 1 percent by weight, particularly when the same is combined with a binder, e.g. 35 weight percent of alumina. The amount of magnesium oxide can be as high as about 25 percent by weight or more depending on the amount and type of binder present. Preferably, the amount of magnesium oxide added to the zeolite is between about 1 and about 15 percent by weight.

Boron oxide is also an effective modifying component. Representative boron-containing compounds include boric acid, trimethylborate, boron hydride, boron oxide, boron sulfide, butylboron dimethoxide, butylboronic acid, dimethylboric anhydride, hexamethylborazine, phenylboric acid, triethylborane, tetramethylammonium borohydride, triphenyl boron and allylborate.

Reaction of the zeolite with the boron compound is effected by contacting the zeolite with such compound. Where the treating boron compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the boron-containing compound is, for example, trimethylborate, a hydrocarbon solvent such as n-octane may be employed. The boron-containing compound may be used without a solvent, i.e., may be used as a neat liquid. Where the boron-containing compound is in the gaseous phase, such as where gaseous diborane is employed, the treating compound can be used by itself or can be used in admixture with a gaseous diluent inert to the boton-containing compound and the zeolite such as nitrogen or helium or with an organic solvent, such as octane.

Prior to reacting the zeolite with the boron-containing compound, the zeolite may be dried. Drying can be effected in the presence of air. Elevated temperatures may be employed. However, the temperature should not be such that the crystal structure of the zeolite is destroyed.

Heating of the boron-containing catalyst subsequent to preparation and prior to use is also preferred. The heating can be carried out in the presence of oxygen, for example, air. Heating can be at a temperature of about 150° C. However, higher temperatures, i.e. up to about 500° C. are preferred. Heating is generally carried out for 3-5 hours but may be extended to 24 hours or longer. While heating temperatures above about 500° C. can be employed, they are not necessary. At temperatures of about 1000° C., the crystal structure of the zeolite tends to deteriorate.

The amount of boron incorporated with the zeolite should be at least about 0.2 percent by weight. However, it is preferred that the amount of boron in the zeolite be at least about 1 percent by weight when the same is combined with a binder, e.g. 35 weight percent of alumina. The amount of boron can be as high as about 20 percent by weight or more depending on the amount and type of binder present. Preferably, the amount of boron added to the zeolite is between about 1.5 and 10 percent by weight. Without being limited by any theoretical considerations, it is contemplated that boron is actually present in the zolite in an oxidized state, such as $B_2O_3$.

Antimony oxide may also be employed as a modifying component. The antimony oxide is present as $Sb_2O_3$ alone or in admixture with other antimony oxides with or without metallic antimony or other antimony compounds being present. In all instances, regardless of the particular state of oxidation of the antimony, its content with respect to the zeolite is computed as if it were present as $Sb_2O_3$. Generally, the amount of $Sb_2O_3$ in the composite catalyst will be between about 6 and about 40 weight percent and preferably between about 10 and about 35 weight percent. Antimony derivatives which may be used include: the hydrides $SbH_3$; the halides $MX_3$, $MX_5$ (M = Sb, X = F, Cl, Br, I); organic alkyl and aryl stibines and their oxides $R_3Sb$, $R_5Sb$, $R_xSb=O$ (R-alkyl or aryl); halogen derivatives $RSbX_2$, $R_2SbX$, $RSbX_4$, $R_2SbX_3$, $R_3SbX_2$, $R_4SbX$; the acids $H_3SbO_3$, $HSbO_2$, $HSb(OH)_6$; organic acids such as $RSbO(OH)_2$, $R_2SbO \cdot OH$, all with R and X defined as above noted. Also included are organic ethers such as $R_2SbOSbR_2$; esters and alcoholates such as $Sb(OOCCH_3)_3$, $Sb(OC_4H_9)_3$, $Sb(OC_2H_5)_3$, $Sb(OCH_3)_3$; amd antimonyl salts as $(SbO)SO_4$, $(SbO)NO_3$, $K(SbO)C_4H_4O_6$, $NaSbO_2 \cdot 3H_2O$.

In some instances, it may be desirable to modify the crystalline aluminosilicate zeolite by combining therewith two or more of the specified oxides. Thus, the zeolite may be modified by prior combination therewith of oxides of phosphorus and boron, oxides of phosphorus and magnesium or oxides of magnesium and boron. When such modification technique is employed, the oxides may be deposited on the zeolite either sequentially or from a solution containing suitable compounds of the elements, the oxides of which are to be combined with the zeolite. The amounts of oxides present in such instance are in the same range as specified above for the individual oxides, with the overall added oxide content being between about 0.5 and about 40 weight percent.

Still another modifying treatment entails steaming of the zeolite by contact with an atmosphere containing from about 5 to about 100 percent steam at a temperature of from about 250° to about 1000° C. for a period of between about 0.25 and about 100 hours and under pressures ranging from sub-atmospheric to several hundred atmospheres to reduce the alpha value thereof to less than 500 and preferably less than 20 but greater than zero.

Another modifying treatment involves precoking of the catalyst to deposit a coating of between about 2 and about 75 and preferably between about 15 and about 75 weight percent of coke thereon. Precoking can be accomplished by contacting the catalyst with a hydrocarbon charge, e.g. toluene, under high severity conditions or alternatively at a reduced hydrogen to hydrocarbon concentration, i.e. 0 to 1 mole ratio of hydrogen to hydrocarbon for a sufficient time to deposit the desired amount of coke thereon.

It is also contemplated that a combination of steaming and precoking of the catalyst under the above conditions may be employed to suitably modify the crystalline aluminosilicate zeolite catalyst.

The conversion process described herein may be carried out as a batch type, semi-continuous or continuous operation utilizing a fixed or moving bed catalyst system. The catalyst after use in a moving bed reactor is conducted to a regeneration zone wherein coke is burned from the catalyst in an oxygen-containing atmosphere, e.g. air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5-2%) is used to burn the coke in a controlled manner so as to limit the temperature to a maximum of around 500°-550° C.

The following examples wherein the modified zeolites are characterized by an activity, in terms of alpha value, of between about 2 and about 5000, and preferably between about 20 and about 500, a xylene sorption capacity greater than 1 gram/100 grams of zeolite and an ortho xylene sorption time for 30 percent of said capacity of greater than 10 minutes, said sorption capacity and sorption time being measured at 120° C. and a xylene pressure of 4.5 ± 0.8 mm. of mercury, will serve to illustrate the catalyst used and method of the invention without limiting the same:

EXAMPLE 1

Twenty grams of the ammonium form of ZSM-5 was suspended in a solution of 6.69 grams of boric acid $H_3BO_3$, in 40 ml. of hot water and allowed to stand overnight at a temperature of about 90° C. The slurry was then placed in an oven at 115° C. and slurried every 30 minutes to maintain uniformity as the water evaporated. After about 2 hours, the bulk of the water was removed and the temperature was increased to 200° C. After about 5 hours, the catalyst weight was 32.4 grams. It was then placed in a furnace, in air, at 500° C., overnight. After cooling the catalyst weight was 21.95 grams, having a theoretical boron content of 4.9 weight percent.

EXAMPLE 2

Toluene and ethylene in a mole ratio of 5.3 (toluene/ethylene) were passed over a catalyst prepared as in Example 1 at a temperature of 450° C. and atmospheric pressure at a weight hourly space velocity of 5.3. Toluene conversion was 6.8 percent (36 percent of theory). Conversion products, on a mole percent basis, were as follows:

| | | |
|---|---|---|
| Benzene | 6 | |
| Ethylbenzene | 3 | |
| Xylenes | 11 | (para:meta:ortho = 69:21:10) |
| Ethyltoluenes | 79 | (para:meta:ortho = 94:6:0) |
| Other C$_9$ | 1 | |

It is noteworthy that ethyltoluenes containing 94 percent of the para isomer were obtained

EXAMPLE 3

Toluene was alkylated with ethylene in the presence of a catalyst of unmodified HZSM-5 having a crystallite size of 0.02 to 0.05 micron. The conditions of reaction and analytical results are summarized in Table III below.

TABLE III

| Run No. | 1 | 2 | 3 | 4 |
|---|---|---|---|---|
| Temp ° C | 300 | 350 | 350 | 350 |
| WHSV | 7.4 | 7.4 | 3.9 | 10.9 |
| Molar Feed Ratio | | | | |
| Toluene/Ethylene | 5 | 5 | 2.5 | 7.6 |
| Stream Time, Hrs. | 1 | 2 | 3 | 4 |
| Conversion Toluene | 15.6 | 18.5 | 36.2 | 13.0 |
| Wt. % Ethylene | 89.0 | 91.4 | 86.7 | 90.5 |
| Ethyl Toluene | | | | |
| Para | 31.95 | 28.96 | 28.54 | 29.61 |
| Meta | 61.40 | 56.83 | 56.56 | 58.07 |
| Ortho | 6.65 | 14.21 | 14.90 | 12.32 |

It is evident from the above results that the unmodified HZSM-5 catalyst is quite unselective for the production of para-ethyltoluene. Equilibrium concentration of ethyltoluene is 31.5 percent para, 50.2 percent meta and 18.3 percent ortho. In the above runs, all three isomers were produced in amounts not substantially different from the thermodynamic equilibrium, illustrating that modification of the zeolite catalyst, as described hereinabove, is essential in achieving the desired selective production of the para isomer.

EXAMPLE 4

Toluene was alkylated with ethylene in the presence of a catalyst of unmodified HZSM-5 having a crystallite size of about 2 microns. The conditions of reaction and analytical results are summarized in Table IV below.

TABLE IV

| Run No. | 1 | 2 |
|---|---|---|
| Temp ° C | 300 | 400 |
| WHSV | 3.8 | 3.8 |
| Molar Feed Ratio | | |
| Toluene/Ethylene | 2.1 | 2.1 |
| Stream Time, Hrs. | 3 | 4 |
| Conversion Toluene | 4.4 | 22.7 |
| Wt. % Ethylene | 18.6 | 79.2 |
| Ethyl Toluene | | |
| Para | 58.1 | 33.0 |
| Meta | 39.9 | 65.4 |
| Ortho | 2.0 | 1.6 |

It will be seen from the above results that the ratio of para to meta isomer changed considerably with temperature and that the amount of ortho isomer was reduced considerably from the equilibrium amount of 18.3 percent.

EXAMPLE 5

A six gram sample of the ammonium form of ZSM-5 was treated with a solution of 7 grams of magnesium acetate tetrahydrate, dissolved in 15 ml of water. The suspension was heated to 92° C. and permitted to stand overnight. The slurry was poured into a crystallizing dish and placed in a 110° C. oven for a period of about 7 hours. The temperature was then increased to about 200° C. and allowed to stand for an additional hour. The catalyst was then placed in a furnace at 500° C. overnight. The weight of the catalyst at the end of this treatment was 6.68 grams. Analysis showed it to have an Mg content of 10.1 weight percent.

EXAMPLE 6

Toluene was alkylated with ethylene in the presence of the catalyst of Example 5. The conditions of reaction and analytical results are summarized in Table V below.

TABLE V

| Run No. | 1 | 2 | 3 |
|---|---|---|---|
| Temp ° C | 350 | 400 | 450 |
| WHSV | 7.4 | 7.4 | 7.4 |
| Molar Feed Ratio | | | |
| Toluene/Ethylene | 5.1 | 5.1 | 5.1 |
| Stream Time, Hrs. | 1 | 2 | 3 |
| Conversion Toluene | 12.6 | 13.2 | 10.0 |
| Wt. % Ethylene | 65.2 | 60.3 | 43.6 |
| Ethyl Toluene | | | |
| Para | 98.99 | 98.38 | 97.83 |
| Meta | 1.01 | 1.62 | 2.17 |
| Ortho | 0 | .027 | .049 |

From the above results, it will be seen that the selectivity to para-xylene was exceptionally high, with only minute amounts of the ortho isomer being produced.

EXAMPLE 7

HZSM-5 having a crystallite size of 0.02 to 0.05 micron was mixed with 35 weight percent alumina binder and extruded to produce a 1/16" cylindrical particle. A ten gram sample of this extrudate was soaked overnight at room temperature in a solution of 8 grams of 85% phosphoric acid in 10 ml of water. The resulting product was filtered, dried at 120° C. for about 2 hours and calcined at 500° C. for approximately an additional 2 hours. Ten grams of the phosphorus impregnated extrudaate was then soaked at room temperature overnight in a solution of 25 grams of magnesium acetate tetrahydrate in 20 ml of water. It was then filtered, dried at 120° C. for about 2 hours and then placed in a furnace at 500° C. for approximately 2 hours. The resulting product contained 4.18 weight percent phosphorus and 7.41 weight percent magnesium.

EXAMPLE 8

Toluene was alkylated with ethylene in the presence of the catalyst of Example 7. The conditions of reaction and analytical results are summarized in Table VI below.

TABLE VI

| Run No. | 1 | 2 | 3 | 4 | 5 | 6 | 7 |
|---|---|---|---|---|---|---|---|
| Temp ° C | 300 | 350 | 350 | 350 | 400 | 400 | 450 |
| WHSV | 7.4 | 7.4 | 3.9 | 3.9 | 3.9 | 3.9 | 3.9 |
| Molar Feed Ratio Toluene/Ethylene | 5.1 | 5.1 | 2.5 | 2.5 | 2.5 | 2.5 | 2.5 |
| Stream Time, Hrs. | 1 | 2 | 3 | 4 | 5 | 6 | 7 |
| Conversion Toluene | 2.4 | 7.1 | 8.2 | 9.2 | 8.0 | 20.1 | 13.2 |
| Wt. % Ethylene | 1.6 | 29.3 | 17.2 | 55.1 | 12.7 | 59.9 | 2.1 |
| Ethyl Toluene Para | 100 | 100 | 99.2 | 98.6 | 98.04 | 98.96 | 98.84 |
| Meta | — | — | .8 | 1.4 | 1.88 | 1.04 | 1.16 |
| Ortho | — | — | — | — | .08 | .04 | — |

Catalyst calcined between runs 3 and 4 and between runs 5 and 6.

It will be evident from the above results that the catalyst employed was extremely selective in achieving production of para ethyltoluene.

EXAMPLE 9

A 12 gram sample of the ammonium form of ZSM-5 having a crystallite size of 0.02 to 0.05 micron was suspended in a solution of 3.21 grams of boric acid and 0.45 gram of 85 percent phosphoric acid dissolved in 25 ml of water. The suspension was allowed to stand overnight at a temperature of 85° C. and thereafter placed in an oven at 110° C. for approximately 6 hours. It was then placed in a furnace at 500° C. overnight. The product catalyst weighed 12.62 grams and contained 4 weight percent of boron (theory) and 1 weight percent of phosphorus (theory).

EXAMPLE 10

Toluene was alkylated with ethylene in the presence of the catalyst of Example 9. The conditions of reaction and analytical results are summarized in Table VII below.

TABLE VII

| Run No. | 1 | 2 |
|---|---|---|
| Temp ° C | 350 | 350 |
| WHSV | 7.4 | 4.0 |
| Molar Feed Ratio Toluene/Ethylene | 4.5 | 2.3 |
| Stream Time, Hrs. | 1 | 2 |
| Conversion Toluene | 13.3 | 24.5 |
| Wt. % Ethylene | 63.0 | 64.3 |
| Ethyl Toluene Para | 82.0 | 76.8 |
| Meta | 17.9 | 23.1 |
| Ortho | .127 | .094 |

From the above results, it is evident that extremely small amounts of the ortho isomer were obtained, even though a significant amount of meta was produced, along with a substantial amount of the desired para isomer.

EXAMPLE 11

A 12 gram sample of the ammonium form of ZSM-5 having a crystallite size of about 2 micron was suspended in a solution of 14 grams of magnesium acetate tetrahydrate and 0.8 gram of boric acid dissolved in 25 ml of water. The suspension was heated to 88° C., permitted to stand overnight and then heated in an oven at 110° C. for a period of about 8 hours. It was thereafter placed in a furnace at 500° C. overnight. The weight of the resulting catalyst product was 14.93 grams. It had a magnesium content (theory) of 9.3 weight percent and a boron content (theory) of 2.6 weight percent.

EXAMPLE 12

The catalyst of Example 11 was used to alkylate toluene with ethylene. The conditions of reaction and analytical results are summarized in Table VIII below.

TABLE VIII

| Run No. | 1 | 2 | 3 | 4 |
|---|---|---|---|---|
| Temp ° C | 350 | 350 | 400 | 400 |
| WHSV | 7.4 | 4.0 | 7.4 | 4.0 |
| Molar Feed Ratio Toluene/Ethylene | 4.5 | 2.2 | 4.5 | 2.2 |
| Stream Time, Hrs. | 1 | 2 | 3 | 4 |
| Conversion Toluene | 8.7 | 8.6 | 4.9 | 10.6 |
| Wt. % Ethylene | 49.9 | 38.2 | 25.9 | 40.1 |
| Ethyl Toluene Para | 94.8 | 94.1 | 91.0 | 90.6 |
| Meta | 5.2 | 5.9 | 9.0 | 9.4 |
| Ortho | — | — | — | — |

It will be evident from the above results that very high yields of para ethyltoluene were obtained, with no ortho ethyltoluene being detected in the product mixture.

EXAMPLE 13

A 5.3 gram sample of the hydrogen form of ZSM-5 having a crystallite size of about 2 micron was steamed at 515° C. for a period of 2 hours and a feed rate of 8.8 cc of liquid water per hour. The temperature was then raised to 640° C. Toluene was then fed at a rate of 180 ml per hour for a period of 4 hours and 15 minutes. The temperature was then reduced to 550° C., the catalyst flushed with nitrogen and then cooled to yield a coke-containing product.

EXAMPLE 14

Toluene was alkylated with ethylene in the presence of the catalyst of Example 13. The conditions of reaction and analytical results are summarized in Table IX below.

TABLE IX

| Run No. | 1 | 2 | 3 | 4 |
|---|---|---|---|---|
| Temp ° C | 300 | 350 | 350 | 350 |
| WHSV | 7.4 | 7.4 | 4.0 | 7.4 |
| Molar Feed Ratio Toluene/Ethylene | 5 | 5 | 2.5 | 5 |
| Stream Time, Hrs. | 1 | 2 | 3 | 4 |
| Conversion Toluene | 4.1 | 16.8 | 25.9 | 14.4 |
| Wt. % Ethylene | 24.1 | 76.8 | 67.6 | 65.6 |
| Ethyl Toluene Para | 93.15 | 81.79 | 78.89 | 84.74 |
| Meta | 6.85 | 18.21 | 21.11 | 15.26 |
| Ortho | — | — | — | — |

It will again be evident that high yields of para ethyltoluene were obtained, with no production of ortho ethyltoluene.

EXAMPLE 15

Ethylbenzene was reacted with ethylene in the presence of the catalyst of Example 9. The conditions of reaction and analytical results are summarized in Table X below.

TABLE X

| | |
|---|---|
| Temp ° C | 350 |
| WHSV | 3.9 |
| Molar Feed Ratio (Ethylbenzene/Ethylene) | 1.9 |
| Stream Time, Hrs. | 8 |
| Conversion Wt. % Ethylbenzene | 30.2 |
| Ethylene | 71.2 |
| Diethylbenzene Para | 81.65 |
| Meta | 18.35 |
| Ortho | — |

It will be seen from the above results that the major product is para diethylbenzene and that no ortho isomer was formed.

EXAMPLE 16

Ethylbenzene and ethylene were reacted in the presence of the catalyst of Example 7. The reaction conditions employed and the liquid products observed are summarized in Table XI below.

TABLE XI

| Run No. | Temp, °C | WHSV EB/C₂H₄ | EB Conv, % | Selectivity, Wt % | | | | Diethylbenzene | | | |
|---|---|---|---|---|---|---|---|---|---|---|---|
| | | | | Benzene | Toluene | Xylene | ET | para | meta | ortho | Ar₉+ |
| 1 | 350 | 3.5/.4 | 9.7 | 7.9 | 2.7 | .5 | 1.7 | 85.7 | 0 | 0 | 1.5 |
| 2 | 350 | 3.5/.8 | 6.0 | 7.7 | — | — | — | 91.5 | .8 | 0 | — |
| 3 | 400 | 3.5/1.2 | 6.3 | 12.0 | 3.1 | .7 | .6 | 82.6 | 1.2 | 0 | — |

EXAMPLE 17

Toluene was alkylated with ethyl alcohol in the presence of the catalyst of Example 9. The reaction conditions and analytical results are summarized in Table XII.

TABLE XII

| | |
|---|---|
| Temp ° C | 500 |
| WHSV Toluene | 5.0 |
| Ethyl Alcohol | 0.5 |
| Stream Time, Hrs. | 4 |
| Conversion Wt. % Toluene | 6.8 |
| Ethyl Alcohol | 100 |
| Ethyltoluene Para | 85.5 |
| Meta | 14.5 |
| Ortho | — |

It is again seen from the above results that para ethyltoluene was selectively produced, with no formation of the ortho isomer.

EXAMPLE 18

A 10 gram sample of HZSM-5 was suspended in a solution of 3.25 grams of 85% phosphoric acid in 150 ml of methanol. The suspension was allowed to reflux gently overnight and then placed in an oven at 150° C. for approximately 3 hours. Thereafter, a sample of this catalyst was calcined at 500° C. in air for 4 hours. The product obtained had a phosphorus content of 7.82 weight percent.

EXAMPLE 19

Toluene was alkylated with ethylene using the catalyst of Example 18. The reaction conditions and analytical results are summarized in Table XIII.

TABLE XIII

| Run No. | 1 | 2 | 3 |
|---|---|---|---|
| Temp ° C | 400 | 450 | 500 |
| WHSV | 7.4 | 3.9 | 3.9 |
| Molar Feed Ratio Toluene/Ethylene | 5 | 2.5 | 2.5 |
| Stream Time, Hrs. | 1 | 2 | 3 |
| Conversion Wt. % Toluene | 0.17 | 5.5 | 3.7 |
| Ethyl Toluene Para | 80 | 84.6 | 77.8 |
| Meta | 20 | 15.4 | 22.2 |
| Ortho | — | — | — |

High selectivity for para ethyltoluene is evident from the above results.

We claim:

1. Process for effecting ethylation of a mono alkyl benzene wherein the alkyl substituent contains 1 or 2 carbon atoms which comprises contacting said mono alkyl benzene, under conversion conditions, with ethylene in the presence of a catalyst comprising a crystalline aluminosilicate zeolite, which zeolite is characterized by an activity, in terms of alpha value of between about 2 and about 5000, a xylene sorption capacity greater than 1 gram/100 grams of zeolite and an ortho xylene sorption time for 30 percent of said capacity of greater than 10 minutes, said sorption capacity and sorption time being measured at 120° C. and a xylene pressure of 4.5 ± 0.8 mm. of mercury, said crystalline aluminosilicate zeolite having a silica to alumina ratio of at least about 12 and a constraint index within the approximate range of 1 to 12 to yield a resulting product in which the para ethyl derivative of said mono alkyl benzene is present in an amount greater than the thermodynamic equilibrium concentration thereof in the total dialkyl substituted benzenes produced.

2. The process of claim 1 wherein the mono alkyl benzene is toluene.

3. The process of claim 1 wherein the mono alkyl benzene is ethylbenzene.

4. The process of claim 1 wherein said conversion conditions include a temperature between about 250 and about 600° C., a pressure between about 0.1 and about 100 atmospheres utilizing a feed weight hourly space velocity between about 0.1 and about 100 and a molar feed ratio of mono alkyl benzene/ethylene agent between about 1 and about 10.

5. The process of claim 1 wherein the crystalline aluminosilicate zeolite has undergone prior modification by combining therewith between about 0.5 and about 40 weight percent of at least one oxide selected from the group consisting of the oxides of phosphorus, antimony, boron and magnesium.

6. The process of claim 1 wherein the crystalline aluminosilicate zeolite has undergone prior modification by combining therewith between about 1 and about 25 weight percent of an oxide of phosphorus.

7. The process of claim 1 wherein the crystalline aluminosilicate zeolite has undergone prior modification by combining therewith between about 1 and about 25 weight percent of an oxide of magnesium.

8. The process of claim 1 wherein the crystalline aluminosilicate zeolite has undergone prior modification by combining therewith between about 1 and about 20 weight percent of an oxide of boron.

9. The process of claim 1 wherein the crystalline aluminosilicate zeolite has undergone prior modification by combining therewith between about 6 and about 40 weight percent of an oxide of antimony.

10. The process of claim 1 wherein the crystalline aluminosilicate zeolite has undergone prior modification by steaming at a temperature between about 250° and about 1000° C. for a period of between about 0.5 and about 100 hours.

11. The process of claim 10 wherein the steamed catalyst has deposited thereon between about 2 and about 75 weight percent of coke thereon.

12. The process of claim 1 wherein the crystalline aluminosilicate zeolite has undergone prior modification by precoking to deposit between about 2 and about 75 weight percent of coke thereon.

13. The process of claim 1 wherein said crystalline aluminosilicate zeolite is ZSM-5.

14. The process of claim 13 wherein said ZSM-5 is admixed with a binder therefor.

15. The process of claim 1 wherein said crystalline aluminosilicate zeolite is admixed with a binder therefor.

* * * * *

Disclaimer 4,086,287.—*Warren W. Kaeding*, Westfield; *Lewis B. Young*, Kendall Park, both of N. J. SELECTIVE ETHYLATION OF MONO ALKYL BENZENES. Patent dated Apr. 25, 1978. Disclaimer filed Jan. 27, 1988, by the assignee, Mobil Oil Corp.

The term of this patent subsequent to April 25, 1995, has been disclaimed.
[*Official Gazette October 31, 1989*]